(12) United States Patent
Neubauer et al.

(10) Patent No.: US 10,660,804 B2
(45) Date of Patent: May 26, 2020

(54) ABSORBENT ARTICLE HAVING LONGITUDINAL DIRECTION FOLDED SIDE REGIONS

(71) Applicant: Kimberly-Clark Worldwide, Inc., Neenah, WI (US)

(72) Inventors: Andrew Edward Neubauer, Neenah, WI (US); Christopher Peter Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 413 days.

(21) Appl. No.: 15/532,540

(22) PCT Filed: Dec. 19, 2014

(86) PCT No.: PCT/US2014/071542
§ 371 (c)(1),
(2) Date: Jun. 2, 2017

(87) PCT Pub. No.: WO2016/099552
PCT Pub. Date: Jun. 23, 2016

(65) Prior Publication Data
US 2017/0326006 A1    Nov. 16, 2017

(51) Int. Cl.
*A61F 13/49*      (2006.01)
*A61F 13/496*     (2006.01)
(Continued)

(52) U.S. Cl.
CPC .. *A61F 13/49001* (2013.01); *A61F 13/15203* (2013.01); *A61F 13/496* (2013.01); *A61F 13/49012* (2013.01); *A61F 13/49015* (2013.01); *A61F 13/49017* (2013.01); *A61F 13/53* (2013.01); *A61F 13/70* (2013.01); *A61F 2013/15406* (2013.01); *A61F 2013/4531* (2013.01); *A61F 2013/49044* (2013.01);
(Continued)

(58) Field of Classification Search
CPC .......... A61F 13/49001; A61F 13/49012; A61F 13/49015; A61F 13/49017; A61F 2013/15365; A61F 2013/1539; A61F 2013/49044; A61F 2013/49068; A61F 2013/49071; A61F 2013/49073
See application file for complete search history.

(56) References Cited

U.S. PATENT DOCUMENTS 3,180,335 A * 4/1965 Baker ............... A61F 13/49001
                                                    604/375
3,430,629 A    3/1969 Murphy
(Continued)

FOREIGN PATENT DOCUMENTS

EP    0 988 014 B1    10/2003

*Primary Examiner* — Catharine L Anderson
(74) *Attorney, Agent, or Firm* — Kimberly-Clark Worldwide, Inc.

(57) ABSTRACT

An absorbent article which can have longitudinal direction folded side regions. The longitudinal direction folded side regions of the absorbent article can provide the absorbent article with a first configuration and a second configuration. In the first configuration, the lateral direction width of each of the front waist edge and the back waist edge can be the same. In the second configuration, the lateral direction width of the front waist edge can be smaller than the lateral direction width of the back waist edge.

17 Claims, 8 Drawing Sheets

(51) Int. Cl.
  *A61F 13/70* (2006.01)
  *A61F 13/15* (2006.01)
  *A61F 13/53* (2006.01)
  *A61F 13/45* (2006.01)

(52) U.S. Cl.
  CPC ............... *A61F 2013/49093* (2013.01); *A61F 2013/530489* (2013.01)

(56) References Cited

U.S. PATENT DOCUMENTS

| | | |
|---|---|---|
| 3,731,688 A | 5/1973 | Litt et al. |
| 3,776,233 A | 12/1973 | Schaar |
| 3,807,402 A | 4/1974 | Miller et al. |
| 3,848,595 A | 11/1974 | Endres |
| 3,860,003 A | 1/1975 | Buell |
| 3,863,637 A | 2/1975 | MacDonald et al. |
| 3,913,578 A | 10/1975 | Schaar |
| 3,929,134 A | 12/1975 | Karami |
| 3,930,501 A | 1/1976 | Schaar |
| 3,938,522 A | 2/1976 | Repke |
| 3,939,837 A * | 2/1976 | Taylor ............... A61F 13/49001 604/385.201 |
| 3,951,150 A | 4/1976 | Schaar |
| 3,999,547 A | 12/1976 | Hernandez |
| 4,108,179 A | 8/1978 | Schaar |
| 4,323,070 A | 4/1982 | Ternstroem et al. |
| 5,584,828 A | 12/1996 | Yamamoto et al. |
| 5,919,179 A | 7/1999 | Faulks et al. |
| 6,045,545 A | 4/2000 | Vandemoortele et al. |
| 6,716,205 B2 | 4/2004 | Popp et al. |
| 2006/0264860 A1 | 11/2006 | Lavon |
| 2008/0312631 A1 | 12/2008 | Okuda |
| 2013/0281954 A1 | 10/2013 | Ishihara et al. |

* cited by examiner

ABSORBENT ARTICLE HAVING LONGITUDINAL DIRECTION FOLDED SIDE REGIONS

BACKGROUND OF THE DISCLOSURE

A primary function of personal care absorbent articles is to absorb and retain body exudates, such as urine and fecal material, with additional desired attributes including low leakage of the body exudates from the absorbent article, a conforming fit of the absorbent article to the wearer's body, and a dry feel to the wearer of the absorbent article.

As the usage of absorbent articles has expanded, their complexity has increased due to the incorporation of additional features serving to enhance their performance and appearance. The costs of the materials and the costs of the manufacturing processes have also increased in conjunction with the increases in complexity. As a result, the prices at which these articles are sold have risen to levels that many potential consumers cannot afford to pay. Attempts have been made in the past to provide an absorbent article at a lower cost for both the consumer and the manufacturer. Such attempts, however, may result in an absorbent article which does not provide the desired attributes. For example, an attempt to provide an absorbent article at a lower cost may result in an absorbent article having materials which may not minimize leakage of body exudates from the absorbent article. As another example, an attempt to provide an absorbent article at a lower cost may result in an absorbent article which may not adequately conform to a wearer's body.

A need exists for a simplified absorbent article. A need exists for an absorbent article which can provide the desired attributes of leakage protection, conformance to body, and a dry feel to the wearer at a lower cost to the consumer and manufacturer.

SUMMARY OF THE DISCLOSURE

In various embodiments, an absorbent article can have an outer cover and a bodyside liner bonded to the outer cover; an absorbent body positioned between the outer cover and the bodyside liner; a front waist region having a front waist edge, a back waist region having a back waist edge, and a crotch region interconnecting the front waist region to the back waist region; a pair of opposing longitudinal direction folded side regions extending from the front waist edge to the back waist edge, each longitudinal direction side region comprising at least one longitudinal direction fold and a portion of each of the longitudinal direction folded side regions is bonded to at least a portion of the bodyside liner in the front waist region; a first configuration in which a lateral direction width of the front waist edge is the same as a lateral direction width of the back waist edge; and a second configuration in which the lateral direction width of the front waist edge is smaller than the lateral direction width of the back waist edge. In various embodiments, each of the longitudinal direction folded side regions is unbonded to the bodyside liner in at least one of the back waist region or the crotch region. In various embodiments, each of the longitudinal direction folded side regions comprises at least one elastic member. In various embodiments, each of the longitudinal direction folded side regions comprises at least a portion of the outer cover. In various embodiments, each of the longitudinal direction folded side regions comprises at least a portion of the outer cover and bodyside liner. In various embodiments, a ratio of the lateral direction width of the front waist edge to the lateral direction width of the back waist edge is 0.5 when the absorbent article is in the second configuration.

In various embodiments, an absorbent article can have an outer cover and a bodyside liner bonded to the outer cover; an absorbent body positioned between the outer cover and the bodyside liner; a front waist region having a front waist edge, a back waist region having a back waist edge, and a crotch region interconnecting the front waist region to the back waist region; a pair of opposing longitudinal direction folded side regions extending from the front waist edge to the back waist edge, each longitudinal direction side region comprising at least one longitudinal direction fold and a portion of each of the longitudinal direction folded side regions is bonded to at least a portion of the bodyside liner in the front waist region; a first configuration in which a ratio of a lateral direction width of the front waist edge to a lateral direction width of the back waist edge is 1; and a second configuration in which a ratio of the lateral direction width of the front waist edge to the lateral direction width of the back waist edge is less than 1. IN various embodiments, each of the longitudinal direction folded side regions is unbonded to the bodyside liner in at least one of the back waist region or the crotch region. In various embodiments, each of the longitudinal direction folded side regions comprises at least one elastic member. In various embodiments, each of the longitudinal direction folded side regions comprises at least a portion of the outer cover. IN various embodiments, each of the longitudinal direction folded side regions comprises at least a portion of the outer cover and bodyside liner. In various embodiments, a ratio of the lateral direction width of the front waist edge to the lateral direction width of the back waist edge is 0.5 when the absorbent article is in the second configuration.

In various embodiments, an absorbent article can have an outer cover and a bodyside liner bonded to the outer cover; an absorbent body positioned between the outer cover and the bodyside liner; a front waist region having a front waist edge, a back waist region having a back waist edge, and a crotch region interconnecting the front waist region to the back waist region; a pair of opposing longitudinal direction folded side regions extending from the front waist edge to the back waist edge, each longitudinal direction side region comprising at least two longitudinal direction folds and a portion of each longitudinal direction folded side regions is bonded to at least a portion of the bodyside liner in the front waist region; a first configuration in which a ratio of a lateral direction width of the front waist edge to a lateral direction width of the back waist edge is 1; and a second configuration in which a ratio of the lateral direction width of the front waist edge to the lateral direction width of the back waist edge is 0.5. In various embodiments, each of the longitudinal direction folded side regions is unbonded to the bodyside liner in at least one of the back waist region or the crotch region. In various embodiments, each of the longitudinal direction folded side regions comprises at least one elastic member. In various embodiments, each of the longitudinal direction folded side regions comprises at least a portion of the outer cover. In various embodiments, each of the longitudinal direction folded side regions comprises at least a portion of the outer cover and bodyside liner.

Figure 1:
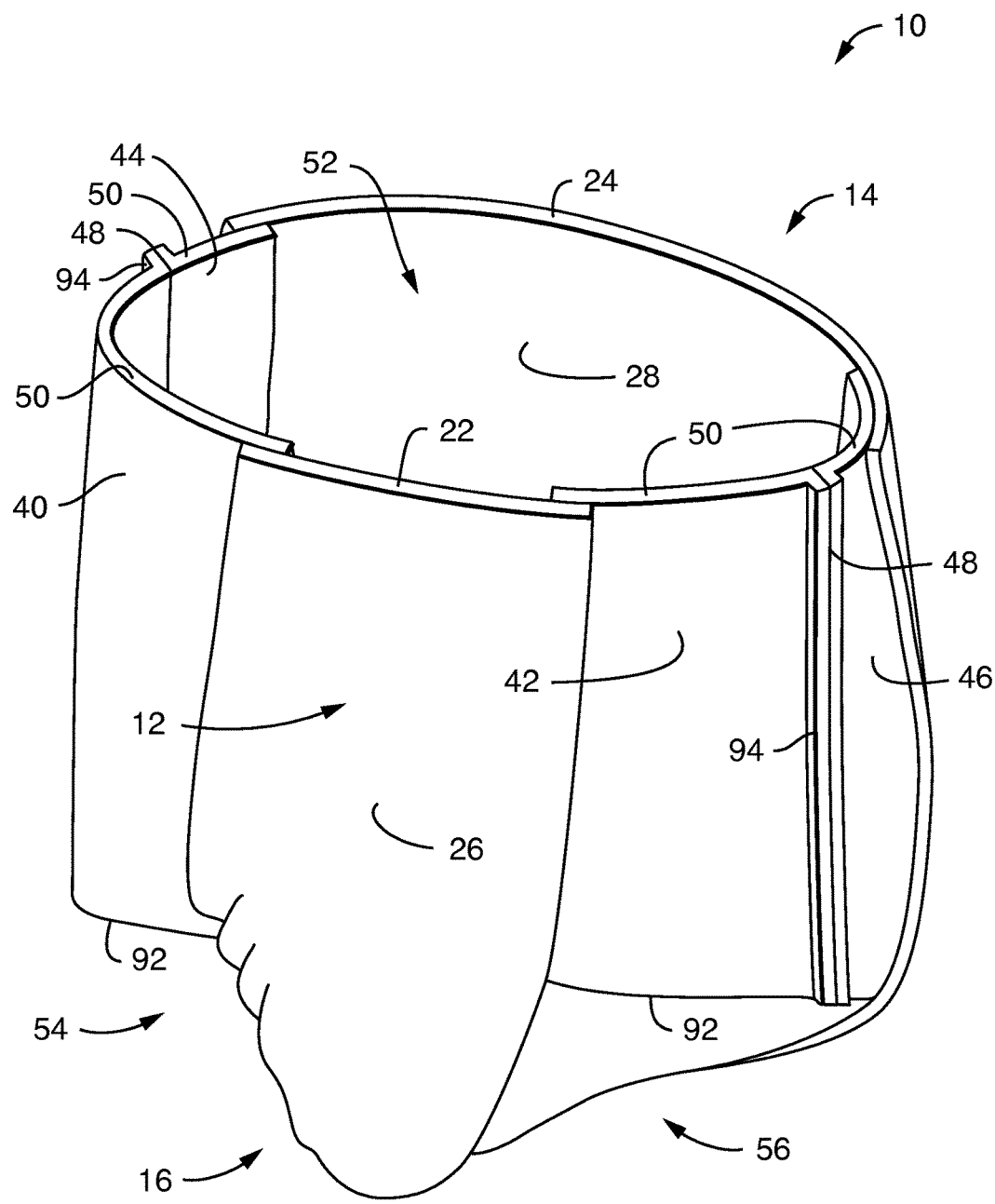
FIG. 1 is a perspective view of an embodiment of an absorbent article.

Repeat use of reference characters in the present specification and drawings is intended to represent the same or analogous features or elements of the disclosure.

DETAILED DESCRIPTION OF THE DISCLOSURE

In various embodiments, the present disclosure is generally directed towards an absorbent article which can have longitudinal direction folded side regions. In various embodiments, the longitudinal direction folded side regions of the absorbent article can provide the absorbent article with a first configuration and a second configuration. In the first configuration, the lateral direction width of each of the front waist edge and the back waist edge can be the same. In the second configuration, the lateral direction width of the front waist edge can be smaller than the lateral direction width of the back waist edge.

Definitions:

The term "absorbent article" refers herein to an article which may be placed against or in proximity to the body (i.e., contiguous with the body) of the wearer to absorb and contain various liquids and solid wastes discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, diaper pants, swim pants, feminine hygiene products, incontinence products, medical garments, other personal care or health care garments, and the like without departing from the scope of the present disclosure.

The term "acquisition layer" refers herein to a layer capable of accepting and temporarily holding liquid body waste to decelerate and diffuse a surge or gush of liquid body waste and to subsequently release the liquid body waste therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Figure 2:
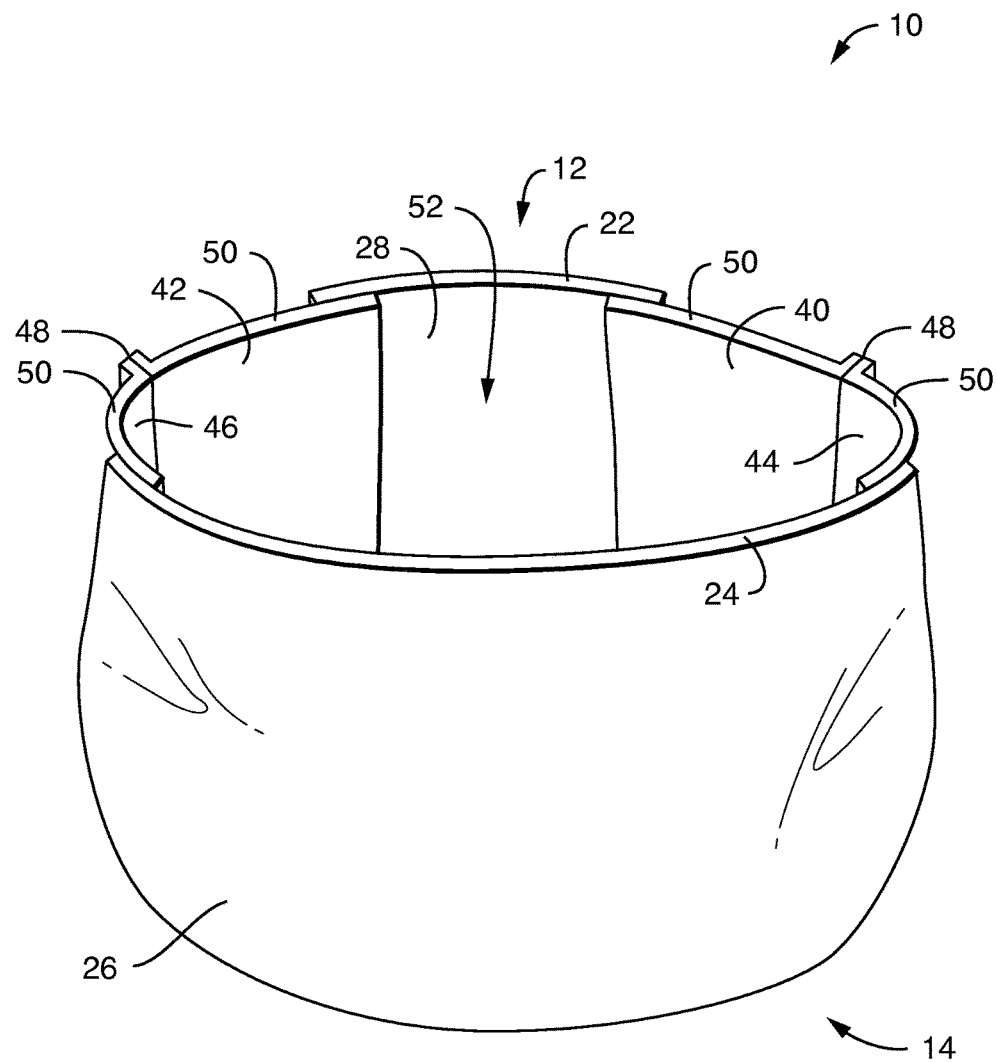
FIG. 2 is a rear view of the absorbent article of FIG. 1.

Absorbent Article:

Referring to FIGS. 1 and 2, a disposable absorbent article 10 of the present disclosure is exemplified in the form of a pant, such as, for example, a training pant in a fully assembled configuration, such as, for example, a wearable configuration. It is to be understood that the present disclosure is suitable for use with various other personal care absorbent articles, such as, for example, diapers, youth pants, diaper pants, swim pants, incontinence products, and feminine hygiene products, without departing from the scope of the present disclosure.

The absorbent article 10 includes a front waist region 12, a back waist region 14, and a crotch region 16 interconnecting the front waist region 12 and the back waist region 14. The absorbent article 10 can have a pair of opposing longitudinal direction side edges, 18 and 20 (shown in FIG. 3). The absorbent article 10 can have a pair of opposing waist edges, respectively designated front waist edge 22 and back waist edge 24. The front waist region 12 can be contiguous with the front waist edge 22 and the back waist region 14 can be contiguous with the back waist edge 24. The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10 that, when worn, is positioned between the legs of the wearer and can partially cover the lower torso of the wearer.

The absorbent article 10 can include an outer cover 26 and a bodyside liner 28. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length, or longitudinal direction, and a width, or lateral direction, which can coincide with the length and width of the absorbent article 10. The longitudinal direction and the lateral direction of the absorbent article 10, and of the materials which form the absorbent article 10, can provide the X-Y planes, respectively, of the absorbent article 10 and of the materials which form the absorbent article 10.

Figure 3:
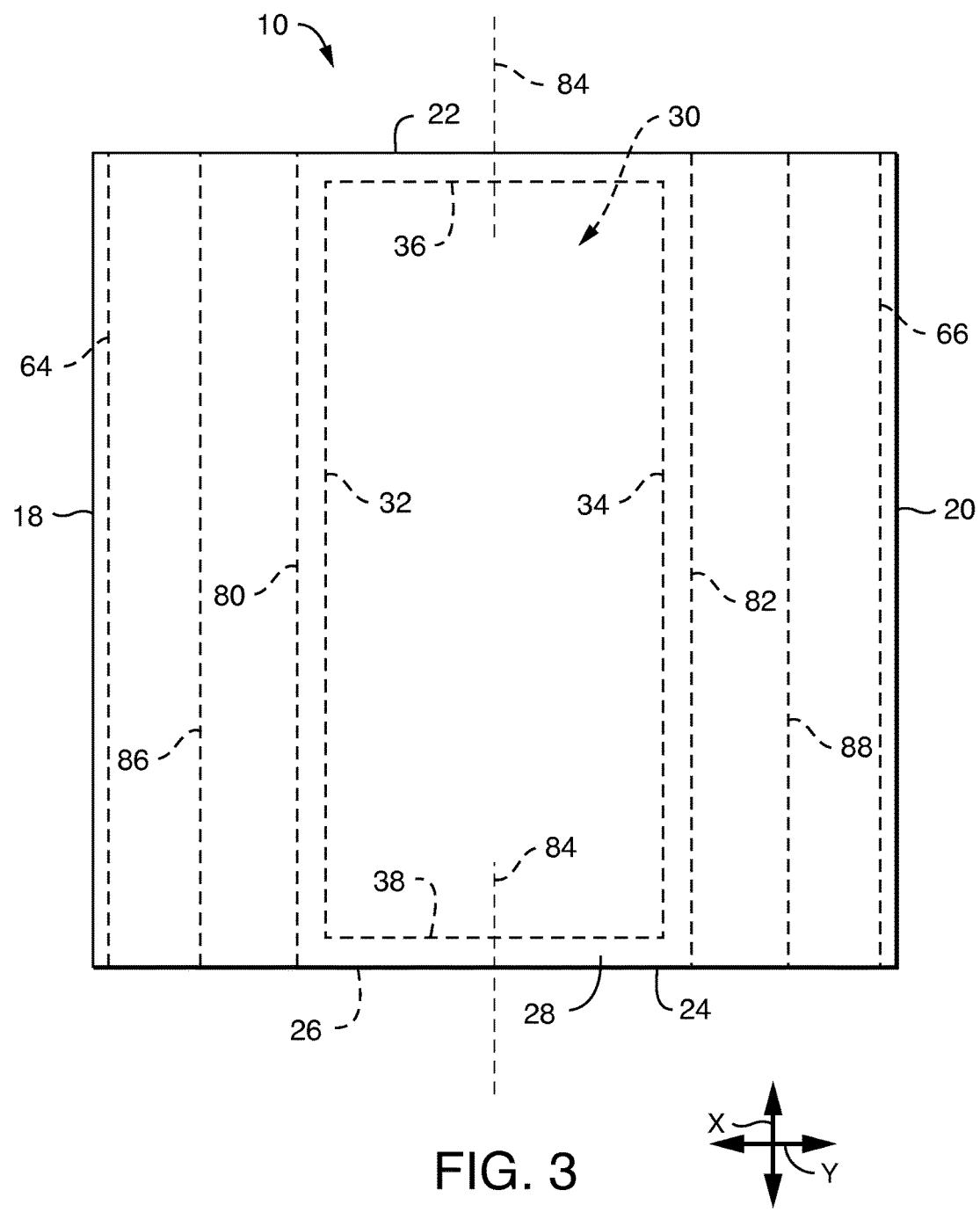
FIG. 3 is a top plan view of the absorbent article of FIG. 1 in an unfastened, unfolded and laid flat condition and showing the surface of the absorbent article that faces the wearer.
Figure 4:
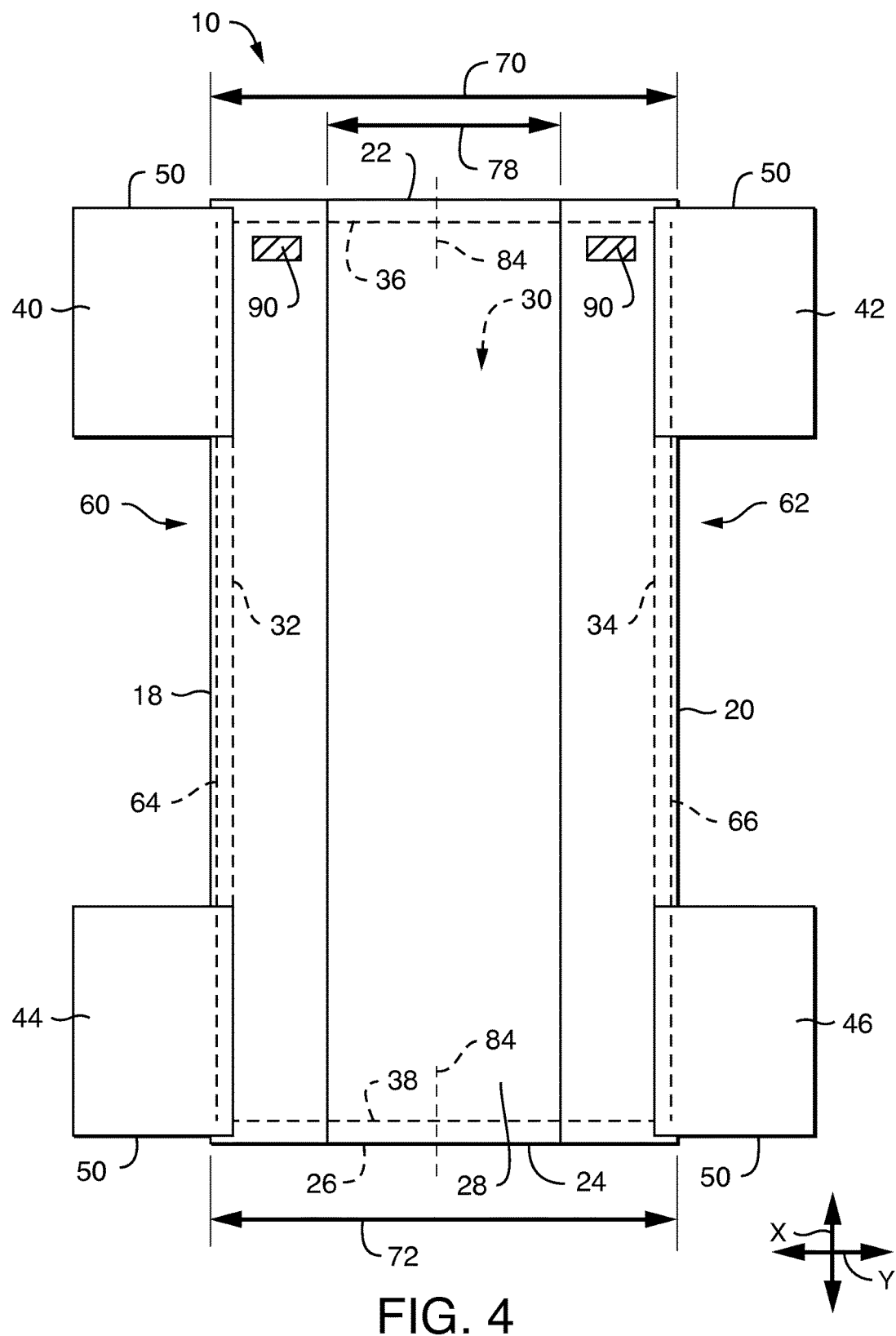
FIG. 4 is a top plan view of an embodiment of the absorbent article of FIG. 3 in an unfastened and laid flat condition in which the absorbent article has longitudinal direction folded side regions and in which the lateral direction width of the front waist edge is the same as the lateral direction width of the back waist edge.
Figure 6:
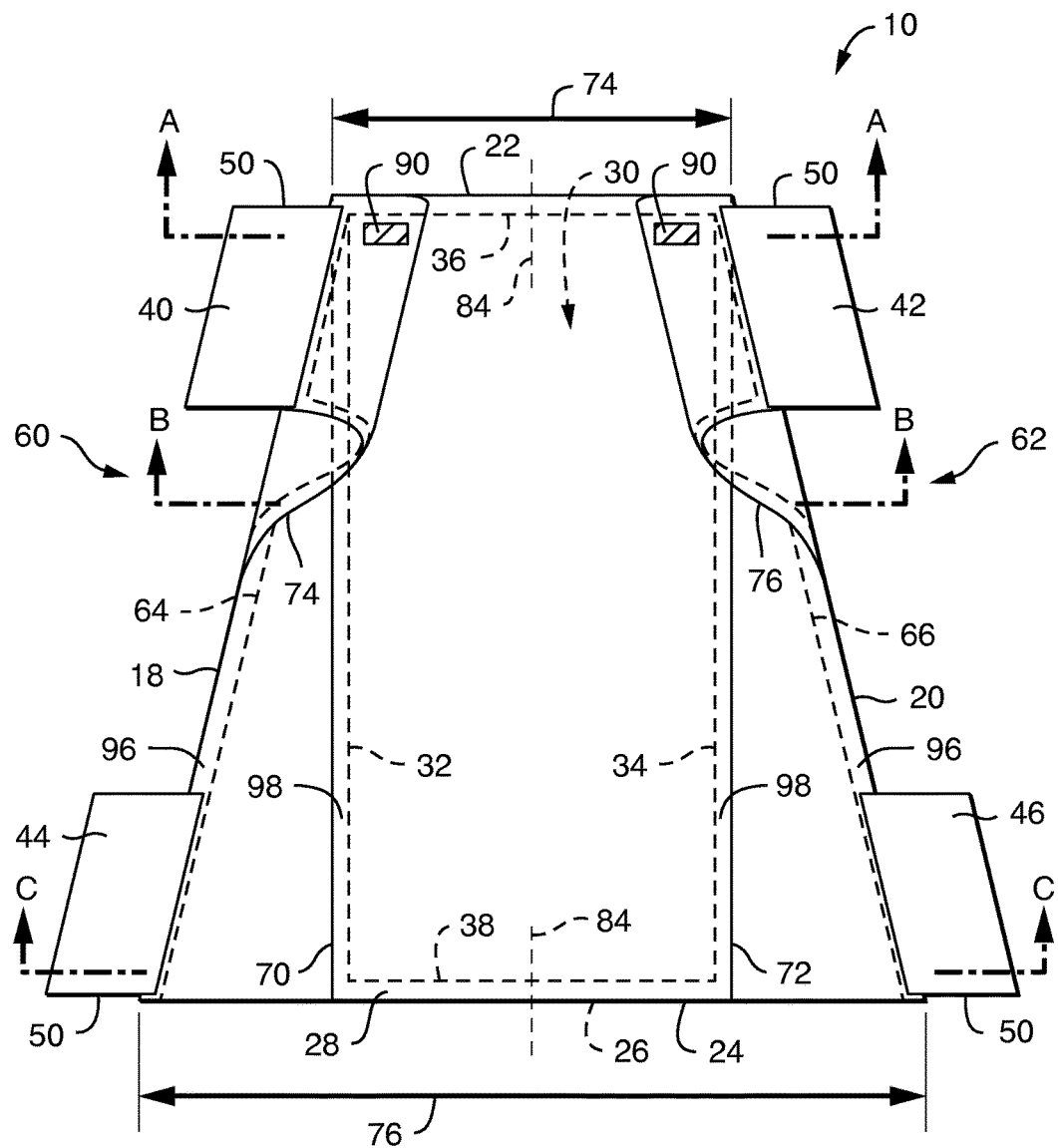
FIG. 6 is a top plan view of an embodiment of the absorbent article of FIGS. 4 and 5 in an unfastened and laid flat configuration in which the lateral direction width of the front waist edge is smaller than the lateral direction width of the back waist edge.

An absorbent body 30 can be disposed between the outer cover 26 and the bodyside liner 28 (such as illustrated in FIGS. 3, 4 and 6). The absorbent body 30 can have longitudinal direction side edges, 32 and 34, respectively, which, in various embodiments, can form portions of the longitudinal direction side edges, 18 and 20, of the absorbent article 10. The absorbent body 30 can have a pair of opposing lateral direction end edges, 36 and 38, which, in various embodiments, can form portions of the waist edges, 22 and 24, respectively, of the absorbent article 10. In various embodiments, the absorbent body 30 can have a longitudinal length and a lateral width that are the same as or less than the longitudinal length and lateral width of the absorbent article 10.

The absorbent article 10 can have a pair of laterally opposed front side panels, 40 and 42, and a pair of laterally opposed back side panels, 44 and 46. The front side panels, 40 and 42, and the back side panels, 44 and 46, of the absorbent article 10 can be bonded to the absorbent article 10 in the respective front and back waist regions, 12 and 14. To assemble the absorbent article illustrated in FIGS. 1 and 2, the front waist region 12 can be bonded to the back waist region 14 via the formation of an engagement seam 48 between a front side panel, such as front side panel 40, and a back side panel, such as back side panel 44. Each of the front side panels, 40 and 42, and each of the back side panels, 44 and 46, can have a waist end edge 50 disposed toward a longitudinal end of the absorbent article 10. The waist edges, 22 and 24, and the waist end edges 50 of each of the side panels, 40, 42, 44 and 46, are configured to encircle the waist of the wearer and together at least partially define the central waist opening 52. When worn, the absorbent article 10 has a pair of leg openings, 54 and 56.

Figure 5:
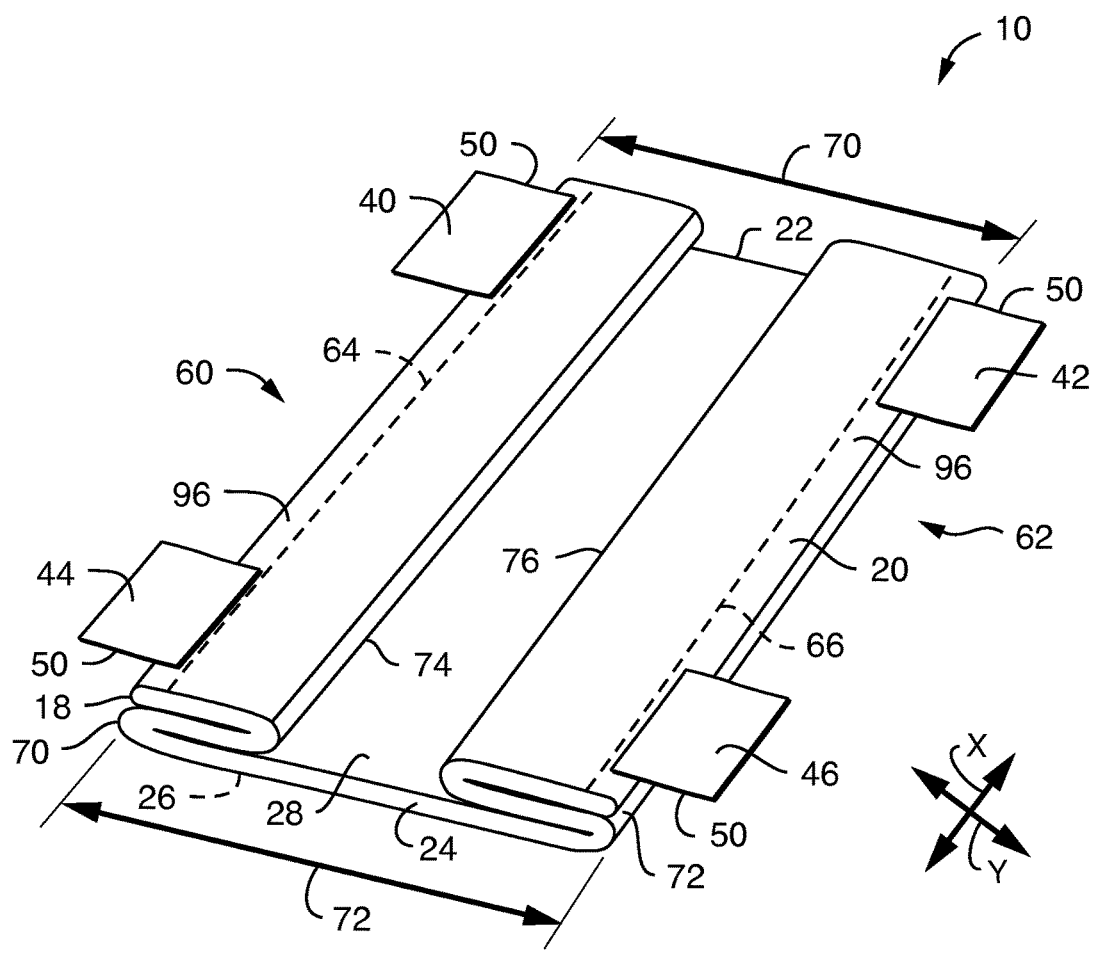
FIG. 5 is a perspective view of the absorbent article of FIG. 4.

The absorbent article 10 can be configured to contain and/or absorb liquid and solid wastes discharged from the wearer. The absorbent article 10 can have an opposing pair of longitudinal direction folded side regions, 60 and 62. Each of the longitudinal direction folded side regions, 60 and 62, can be incorporated into the absorbent article 10 by incorporating at least one longitudinal direction fold into at least one of the materials which forms the absorbent article 10. The longitudinal direction side regions, 60 and 62, can provide the absorbent article 10 with a first configuration and a second configuration. In the first configuration, each of the longitudinal direction folded side regions, 60 and 62, are in a fully folded configuration and the lateral direction width 70 of the front waist edge 22 is the same as the lateral direction width 72 of the back waist edge 24 (such as illustrated in FIG. 5). In the second configuration, the absorbent article 10 can undergo expansion in the lateral direction. As such, the lateral direction width 74 of the front waist edge 22 is smaller than the lateral direction width 76 of the back waist edge 24 (such as illustrated in FIG. 6). The longitudinal direction folded side regions, 60 and 62, can be configured to provide a barrier to the lateral flow of body exudates. An elastic member, 64 and 66, can be operatively bonded to each longitudinal direction side region, 60 and 62, respectively, in any suitable manner known in the art. The elasticized longitudinal direction folded side regions, 60 and 62, can at least partially define a partially unattached area that can assume an upright configuration in at least the crotch region 16 of the absorbent article 10 to form a seal against the wearer's body. Without being bound by theory, it is believed that in various embodiments, the longitudinal direction folded side regions, 60 and 62, can provide the function of containment flaps in the crotch region 16 and can perform the function of elasticized leg cuffs in the back waist region 14.

Additional details regarding each of these elements of the absorbent article 10 described herein can be found below and with reference to FIGS. 1-7.

Outer Cover:

The outer cover 26 can be breathable and/or liquid impermeable. The outer cover 26 can be elastic, stretchable or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, the outer cover 26 can be a single layer of a liquid impermeable material. In an embodiment, the outer cover 26 can be suitably stretchable, and more suitably elastic, in at least the lateral or circumferential direction of the absorbent article 10. In an embodiment, the outer cover 26 can be stretchable, and more suitably elastic, in both the lateral and the longitudinal directions. In an embodiment, the outer cover 26 can be a multi-layered laminate in which at least one of the layers is liquid impermeable. In an embodiment, the outer cover 26 may be a two layer construction, including an outer layer constructed of a liquid permeable material and an inner layer constructed of liquid impermeable material bonded together by a laminate adhesive. Suitable laminate adhesives can be applied continuously or intermittently as beads, a spray, parallel swirls, or the like. Suitable adhesives can be obtained from Bostik Inc. of Wauwatosa, Wis., U.S.A. It is to be understood that the inner layer can be bonded to the outer layer utilizing ultrasonic bonds, thermal bonds, pressure bonds, or the like.

The liquid permeable outer layer of the outer cover 26 can be any suitable material and may be one that provides a generally cloth-like texture to the wearer. An example of such material can be a 100% polypropylene bonded-carded web with a diamond bond pattern available from Sandler A.G., Germany such as 30 gsm Sawabond 4190® or equivalent. Another example of material suitable for use as an outer layer of an outer cover 26 can be a 20 gsm spunbond polypropylene non-woven web. The outer layer may also be constructed of the same materials from which the bodyside liner 28 is constructed as described herein. It is to be understood that it is not necessary for the outer layer of the outer cover 26 to be liquid permeable.

The liquid impermeable inner layer of the outer cover 26 can be either vapor permeable (i.e., "breathable") or vapor impermeable. The inner layer may be manufactured from a thin plastic film, although other liquid impermeable materials may also be used. The liquid impermeable inner layer (or the liquid impermeable outer cover 26 where the outer cover 26 is of a single-layer construction) can inhibit liquid body waste from leaking out of the absorbent article 10 and wetting articles, such as bed sheets and clothing, as well as the wearer and caregiver. An example of a material for an inner layer can be a printed 19 gsm XP-8695H or 8790C film or equivalent commercially available from Berry Corporation, Schaumburg, Ill., U.S.A.

Where the outer cover 26 is of a single layer construction, it can be embossed and/or matte finished to provide a more cloth-like appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 30 can be suitably constructed to be generally compressible, conformable, pliable, non-irritating to the wearer's skin and capable of absorbing and retaining liquid body waste, such as urine. The absorbent body 30 can be manufactured in a wide variety of sizes and shapes (for example, rectangular, trapezoidal, T-shape, I-shape, hourglass shape, etc.) and from a wide variety of materials. The size and the absorbent capacity of the absorbent body 30 should be compatible with the size of the intended wearer and the liquid loading imparted by the intended use of the absorbent article 10. Additionally, the size and the absorbent capacity of the absorbent body 30 can be varied to accommodate wearers ranging from infants to adults.

The absorbent body 30 may have a length ranging from about 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 30 may have a crotch width ranging from about 50, 55, 60, 65, or 70 mm to about 75, 80, 85, 90, 95, 100, 105, 110, 115, 120, 125, 130, 140, 150, 160, 170 or 180 mm. The width of the absorbent body 30 located within the front waist region 12 and/or the back waist region 14 of the absorbent article 10 may range from about 80, 85, 90, or 95 mm to about 100, 105, 110, 115, 120, 125 or 130 mm. As noted herein, the absorbent body 30 can have a length and width that can be less than the length and width of the absorbent article 10.

In an embodiment, the absorbent article 10 can be a diaper having the following ranges of lengths and widths of an absorbent body 30 having an hourglass shape: the length of the absorbent body 30 may range from about 200, 210, 220, 225, 240 or 250 mm to about 260, 280, 300, 310, 320, 330, 340, 350, 355, 360, 380, 385, or 390 mm; the width of the absorbent body 30 in the crotch region 16 may range from about 50, 55, or 60 mm to about 65, 70, 75, or 80 mm; the width of the absorbent body 30 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 30 having an hourglass shape: the length of the absorbent body 30 may range from about 400, 410, 420, 440 or 450 mm to about 460, 480, 500, 510 or 520 mm; the width of the absorbent body 30 in the crotch region 16 may range from about 50, 55, or 60 mm to about 65, 70, 75, or 80 mm; the width of the absorbent body 30 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 30 having a rectangular shape: the length of the absorbent body 30 may range from about 400, 410 or 415 to about 425 or 450 mm; the width of the absorbent body 30 in the crotch region 16 may range from about 90, or 95 mm to about 100, 105, or 110 mm. It should be noted that the absorbent body 30 of an adult incontinence garment may or may not extend into either or both the front waist region 12 or the back waist region 14 of the absorbent article 10.

The absorbent body 30 can have two surfaces such as a wearer facing surface and a garment facing surface. Side edges, such as longitudinal side edges, 32 and 34, and such as front and back end edges, 36 and 38, can connect the two surfaces.

In an embodiment, the absorbent body 30 can be composed of a web material of hydrophilic fibers, cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In an embodiment, the absorbent body 30 can be a matrix of cellulosic fluff and superabsorbent hydrogel-forming particles. The absorbent body 30 may be constructed of a single layer of materials, or in the alternative, may be constructed of two layers of materials or more.

In an embodiment in which the absorbent body 30 has two layers, the absorbent body 30 can have a wearer facing layer suitably composed of hydrophilic fibers and a garment facing layer suitably composed at least in part of a high absorbency material commonly known as superabsorbent material. In an embodiment, the wearer facing layer of the absorbent body 30 can be suitably composed of cellulosic fluff, such as wood pulp fluff, and the garment facing layer of the absorbent body 30 can be suitably composed of superabsorbent hydrogel-forming particles, or a mixture of cellulosic fluff and superabsorbent hydrogel-forming particles. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 30 with a lower absorbent capacity in the wearer facing layer than in the garment facing layer.

Various types of wettable, hydrophilic fibers can be used in the absorbent body 30. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

In an embodiment, the cellulosic fluff can include a blend of wood pulp fluff. An example of wood pulp fluff can be "Bowater CoosAbsorb S Fluff Pulp" or equivalent available from Bowater, Greenville, S.C., U.S.A. which is a bleached, highly absorbent sulfate wood pulp containing primarily southern soft wood fibers. The absorbent web can be formed with a dry-forming technique, an air forming technique, a wet-forming technique, a foam-forming technique, or the like, as well as combinations thereof. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than 24 times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 30. In an embodiment, the absorbent body 30 can have at least about 50% by weight of a superabsorbent material. In an embodiment, the absorbent body 30 can have at least about 50, 55, 60, 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 30 can be superposed over the inner layer of the outer cover 26 and can be bonded to the inner layer of the outer cover 26, such as by being bonded thereto with adhesive. However, it is to be understood that the absorbent body 30 may be in contact with, and unbounded with, the outer cover 26 and remain within the scope of this disclosure.

Bodyside Liner:

The bodyside liner 28 of the absorbent article 10 can overlay the absorbent body 30 and the outer cover 26 and can isolate the wearer's skin from liquid waste retained by the absorbent body 30. The bodyside liner 28 may also overlay an acquisition layer and may be bonded to the acquisition layer. In an embodiment, the bodyside liner 28 can extend beyond the absorbent body 30 and/or the acquisition layer to overlay a portion of the inner layer of the outer cover 26 and can be bonded thereto by any method deemed suitable, such as, for example, by being bonded thereto by adhesive, to substantially enclose the absorbent body 30 between the outer cover 26 and the bodyside liner 28. The bodyside liner 28 may be slightly narrower than the outer cover 26, but it is to be understood that the bodyside liner 28 and the outer cover 26 may be of the same dimensions. It is also contemplated that the bodyside liner 28 may not extend beyond the absorbent body 30 and may not be secured to the outer cover 26. The bodyside liner 28 can be suitably compliant, soft feeling, and non-irritating to the wearer's skin and can be less hydrophilic than the absorbent body 30 to provide a relatively dry surface to the wearer and permit liquid body waste to readily penetrate through its thickness.

The bodyside liner 28 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 28. For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a 12 gsm spunbond-meltblown-spunbond substrate having 10% meltblown content applied between the two spunbond layers.

In an embodiment, the bodyside liner 28 can have a basis weight less than about 30 gsm. In an embodiment, the bodyside liner 28 can have a basis weight less than about 30, 28, 26, 24, 22, 20, 18, 16, 14 or 12 gsm. In an embodiment, the bodyside liner 28 can have a basis weight from about 6, 8, 10, 12, 14, 16, or 18 gsm to about 20, 22, 24, 26, 28 or 30 gsm.

Although the outer cover 26 and bodyside liner 28 can include elastomeric materials, it is contemplated that the outer cover 26, the bodyside liner 28 and the absorbent body 30 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions.

Longitudinal Direction Folded Side Regions:

The absorbent article 10 can be configured to contain and/or absorb liquid and solid wastes discharged from the wearer. To provide these attributes, the absorbent article 10 can have an opposing pair of longitudinal direction folded side regions, 60 and 62 (such as illustrated in FIGS. 4-7) to provide a barrier against the flow of urine to the leg openings, 54 and 56. The longitudinal direction folded side regions, 60 and 62, can extend longitudinally from the front waist edge 22 of the absorbent article 10, through the crotch region 16 to the back waist edge 24 of the absorbent article 10.

Each of the longitudinal direction folded side regions, 60 and 62, can be incorporated into the absorbent article 10 by incorporating at least one longitudinal direction fold, such as first longitudinal direction folds, 70 and 72, (illustrated in FIG. 5) into the absorbent article 10 between the longitudinal direction centerline 84 and each of the absorbent article 10 longitudinal direction side edges, 18 and 20. FIG. 3 provides an illustration of the absorbent article 10 in an unfastened, unfolded and laid flat condition and showing the surface of the absorbent article 10 that faces the wearer. To incorporate longitudinal direction folded side region 60 into the absorbent article 10 a first longitudinal direction fold 70 can be incorporated into the absorbent article 10 at fold line 80 which is located between the longitudinal direction centerline 84 and the absorbent article 10 longitudinal direction side edge 18. To incorporate longitudinal direction folded side region 62 into the absorbent article 10 a first longitudinal direction fold 72 can be incorporated into the absorbent article 10 at fold line 82 which is located between the longitudinal direction centerline 84 and the absorbent article 10 longitudinal direction side edge 20. Each of the first longitudinal direction folds, 70 and 72, bring the longitudinal direction side edges, 18 and 20, respectively, of the absorbent article 10 into closer proximity with the longitudinal direction centerline 84. Such first longitudinal direction folds, 70 and 72, can provide longitudinal direction folded side regions, 60 and 62, which can have a C- and a reverse-C-configuration, respectively.

The longitudinal direction folded side regions, 60 and 62, can contain as many folds as deemed suitable. In various embodiments, the longitudinal direction folded side regions, 60 and 62, can have 1, 2, 3, 4, 5 or 6 longitudinal direction folds. Each fold can result in a layer of the longitudinal direction folded side region overlaying another layer of the longitudinal direction folded side region. In various embodiments, each of the layers in a longitudinal direction folded side region can have the same lateral direction width. In various embodiments, at least one of the layers of a longitudinal direction folded side region can have a lateral direction width which can be different from a lateral direction width of another layer within the same longitudinal direction folded side region.

In various embodiments, additional folds, such as second longitudinal direction folds, 74 and 76 (illustrated in FIG. 5), can also be incorporated into each of the longitudinal direction folded side regions, 60 ad 62, respectively. The second longitudinal direction folds, 74 and 76, can be incorporated into the longitudinal direction folded side regions, 60 and 62, at their respective fold lines, 86 and 88 (illustrated in FIG. 3). The second longitudinal direction folds, 74 and 76, can result in longitudinal direction folded side regions, 60 and 62, which can have a Z- and a reverse-Z-configuration, respectively. The second longitudinal direction folds, 74 and 76, can also result in the movement of the longitudinal direction side edges, 18 and 20, away from the longitudinal direction centerline 84 and into closer proximity with the first longitudinal direction folds, 70 and 72.

In various embodiments, the longitudinal direction folded side regions, 60 and 62, can be incorporated into the absorbent article 10 by incorporating folds, such as the first longitudinal direction folds, 70 and 72, and/or second longitudinal direction folds, 74 and 76, into at least one of the materials forming the absorbent article 10. In such embodiments, therefore, the longitudinal direction folded side regions, 60 and 62, can be formed from any of the outer cover 26, the bodyside liner 28, the absorbent body 30, any other material of the absorbent article 10 or combinations thereof. In various embodiments, the longitudinal direction folded side regions, 60 and 62, can be incorporated into the absorbent article 10 by incorporating folds in a portion of the outer cover 26 of the absorbent article 10. In various embodiments, the longitudinal direction folded side regions, 60 and 62, can be incorporated into the absorbent article 10 by incorporating folds, in tandem, in a portion of the outer cover 26 and a portion of the bodyside liner 28. In various embodiments, the longitudinal direction folded side regions, 60 and 62, can be incorporated into the absorbent article 10 by incorporating folds, in tandem, in a portion of each of the outer cover 26, bodyside liner 28 and absorbent body 30. In various embodiments, the longitudinal direction folded side regions, 60 and 62, can be incorporated into an absorbent article 10 by incorporating folds, in tandem, in any of the materials forming the absorbent article 10.

In various embodiments, the longitudinal direction folded side regions, 60 and 62, of the absorbent article 10 can provide the absorbent article 10 with a first configuration (such as illustrated in FIGS. 4 and 5 in an unfastened and laid flat configuration) and a second configuration (such as illustrated in FIG. 6 in an unfastened and laid flat configuration). In the first configuration, which can be a pre-wear configuration, the longitudinal direction folded side regions, 60 and 62, can be in a generally parallel, spaced relation with each other and the lateral direction width 70 of the front waist edge 22 and the lateral direction width 72 of the back waist edge 24 can be the same. In the second configuration, which can be a wearable configuration, the lateral direction width 74 of the front waist edge 22 can be smaller than the lateral direction width 76 of the back waist edge 24.

To facilitate the ability of the absorbent article 10 to transition from the first configuration to the second configuration, a portion of each of the longitudinal direction folded side regions, 60 and 62, can be bonded, such as, for example, at bond location 90, to a portion of the bodyside liner 28 of the absorbent article 10 and the bond location 90 can be in the front waist region 12 of the absorbent article 10. In various embodiments, the bond location 90 can be substantially adjacent to the front waist edge 22 of the absorbent article 10. The bonding of a portion of each of the longitudinal direction folded side regions, 60 and 62, at bond location 90 can occur via adhesive, thermal bonding, ultrasonic bonding, pressure bonding or combinations thereof. To allow for the transition from the first configuration to the second configuration, each of the longitudinal direction folded side regions, 60 and 62, remains unbonded to the bodyside liner 28 in both the back waist region 14 and the crotch region 16 of the absorbent article 10.

In various embodiments, in the first configuration, a ratio of the lateral direction width 70 of the front waist edge 22 to the lateral direction width 72 of the back waist edge 24 is 1. In various embodiments, in the second configuration, a ratio of the lateral direction width 74 of the front waist edge 22 to the lateral direction width 76 of the back waist edge 24 is less than 1. In various embodiments, in the second configuration, a ratio of the lateral direction width 74 of the front waist edge 22 to the lateral direction width 76 of the back waist edge 24 is 0.9, 0.8, 0.7, 0.6, 0.5, 0.4 or 0.3. In various embodiments, in the second configuration, a ratio of the lateral direction width 74 of the front waist edge 22 to the lateral direction width 76 of the back waist edge 24 is 0.5.

Each of the longitudinal direction folded side regions, 60 and 62, can have an elastic member, 64 and 66, respectively, which can be operatively bonded to each longitudinal direction side region, 60 and 62, in any suitable manner known in the art. The elasticized longitudinal direction folded side regions, 60 and 62, can, therefore, at least partially define a partially unattached area that can assume an upright configuration in the crotch region 16 and the back waist region 14 of the absorbent article 10 to form a seal against the wearer's body. For example, each of the longitudinal direction folded side regions, 60 and 62, can be formed by incorporating folds into the outer cover 26 of an absorbent article 10. In such an example, the outer cover can be a bilaminate material and can have a nonwoven layer and a film layer bonded to the nonwoven layer, such as by being bonded thereto by adhesive. An elastic member 64 can be secured by a suitable adhesive between the nonwoven layer and the film layer, generally at a distal end of the outer cover 26. The outer cover 26 can then be folded at least once to form one of the longitudinal direction folded side regions, such as longitudinal direction folded side region 60. In various embodiments, a second fold can be incorporated to provide a longitudinal direction folded side region have a Z-configuration.

The elastic members, 64 and 66, can have two strands of elastomeric material extending longitudinally along the distal ends of the outer cover 26, in generally parallel, spaced relation with each other. The elastic members, 64 and 66, can be secured between the non-woven layer and the film layer of an outer cover 26 while in an elastically contractible condition such that contraction of the strands gathers and shortens the distal ends of the outer cover 26. As a result, the elastic members, 64 and 66, can bias the distal ends 96 of each longitudinal direction folded side region, 60 and 62, toward a position spaced from the proximal end 98 of the longitudinal direction folded side regions, 60 and 62, so that the longitudinal direction folded side regions, 60 and 62, can extend away from the bodyside liner 28 in a generally upright orientation of the longitudinal direction folded side regions, 60 and 62, in the crotch region 16 and the back waist region 14 of the absorbent article 10, when the absorbent article 10 is fitted on the wearer. As such, the longitudinal direction folded side regions, 60 and 62, can perform as a containment flap in the crotch region 16 and has a leg cuff in the back waist region 14 of the absorbent article 10.

Figure 6A:
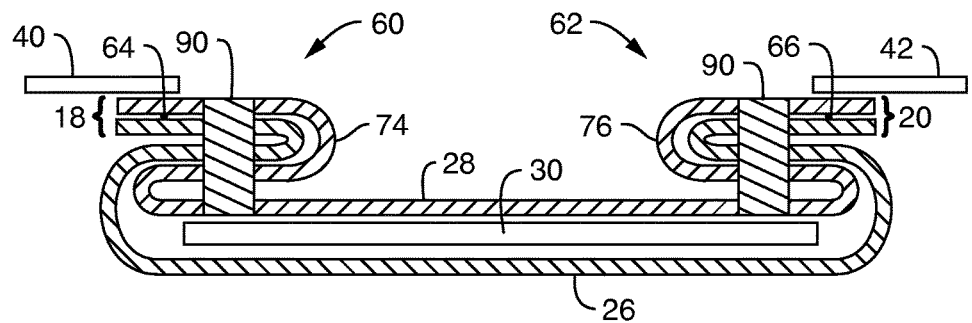
FIGS. 6A, 6B and 6B are cross-sections of the absorbent article of FIG. 6.
Figure 6B:
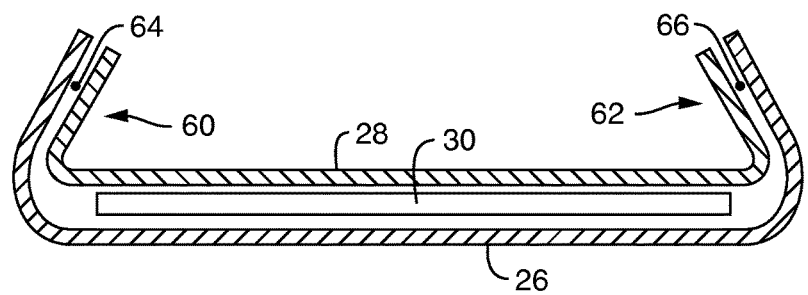
Figure 6C:
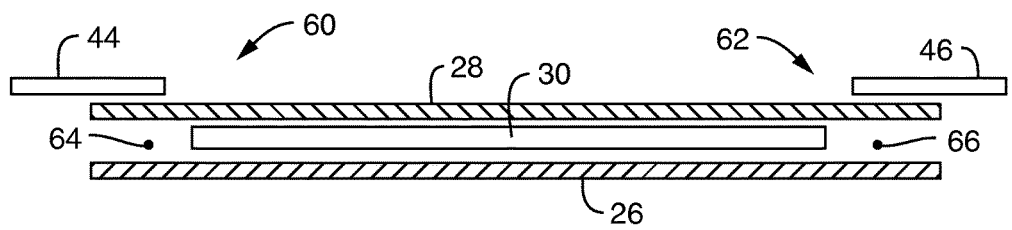

FIG. 6 provides an illustration of an exemplary embodiment of an absorbent article 10 in a second configuration in which the the longitudinal direction folded side regions, 60 and 62, can remain in a folded configuration near the front waist edge 22 of the absorbent article 10 and as the longitudinal direction folded side regions, 60 and 62, continue towards the back waist edge 24 in the second configuration, the distal ends 96 of each of the longitudinal direction folded side regions, 60 and 62, are biased away from the bodyside liner 28. The longitudinal direction folded side regions, 60 and 62, can, therefore, assume an upright configuration in the crotch region 16 and can fully open in the back waist region 14. FIGS. 6A, 6B and 6C are cross-sectional views of the absorbent article of FIG. 6 and can further illustrate the positioning of the longitudinal direction folded side regions, 60 and 62, when the absorbent article 10 can be in a second configuration.

Side Panels:

In an embodiment in which the absorbent article 10 can be a training pant, youth pant, diaper pant, or adult absorbent pant, the absorbent article 10 may have front side panels, 40 and 42, and rear side panels, 44 and 46. The front side panels 40 and 42 and the rear side panels 44 and 46 of the absorbent article 10 can be bonded to the absorbent article 10 in the respective front and back waist regions, 12 and 14, and can extend outwardly beyond the longitudinal side edges, 18 and 20, of the absorbent article 10. The front side panels, 40 and 42, and the back side panels, 44 and 46, can be bonded to the absorbent article 10 either before or after the incorporation of the longitudinal direction folded side regions, 60 and 62, into the absorbent article 10. In an example, the front side panels, 40 and 42, can be bonded to the inner layer of the outer cover 26, such as being bonded thereto by adhesive, by pressure bonding, by thermal bonding or by ultrasonic bonding. These side panels, 40 and 42, may also be bonded to the outer layer of the outer cover 26, such as by being bonded thereto by adhesive, by pressure bonding, by thermal bonding, or by ultrasonic bonding. The back side panels, 44 and 46, may be secured to the outer and inner layers of the outer cover 26 at the back waist region 14 of the absorbent article 10 in substantially the same manner as the front side panels, 40 and 42. Alternatively, the front side panels, 40 and 42, and the back side panels, 44 and 46, may be formed integrally with the absorbent article 10, such as by being formed integrally with the outer cover 26, the bodyside liner 28 or other layers of the absorbent article 10.

For improved fit and appearance, the front side panels, 40 and 42, and the back side panels, 44 and 46, can suitably have an average length measured parallel to the longitudinal axis of the absorbent article 10 that is about 20 percent or greater, and more suitably about 25 percent or greater, of the overall length of the absorbent article 10, also measured parallel to the longitudinal axis. For example, absorbent articles 10 having an overall length of about 54 centimeters, the front side panels, 40 and 42, and the back side panels, 44 and 46, suitably have an average length of about 10 centimeters or greater, and more suitably have an average length of about 15 centimeters. Each of the front side panels, 40 and 42, and back side panels, 44 and 46, can be constructed of one or more individual, distinct pieces of material. For example, each front side panel, 40 and 42, and back side panel, 44 and 46, can include first and second side panel portions (not shown) joined at a seam (not shown), with at least one of the portions including an elastomeric material. Alternatively, each individual front side panel, 40 and 42, and back side panel, 44 and 46, can be constructed of a single piece of material folded over upon itself along an intermediate fold line (not shown).

The front side panels, 40 and 42, and back side panels, 44 and 46, can each have an outer edge 94 spaced laterally from the engagement seam 48, a leg end edge 82 disposed toward the longitudinal center of the absorbent article 10, and a waist end edge 50 disposed toward a longitudinal end of the absorbent article 10. The leg end edge 92 and waist end edge 50 can extend from the longitudinal side edges, 18 and 20, of the absorbent article 10 to the outer edges 94. The leg end edges 92 of the front side panels, 40 and 42, and back side panels, 44 and 46, can form part of the longitudinal side edges, 18 and 20, of the absorbent article 10. The leg end edges 92 can be curved and/or angled relative to the transverse axis to provide a better fit around the wearer's legs. However, it is understood that only one of the leg end edges 92 can be curved or angled, such as the leg end edge 92 of the back waist region 14, or neither of the leg end edges 92 can be curved or angled, without departing from the scope of this disclosure. The waist end edges 50 can be parallel to the transverse axis. The waist end edges 20 of the front side panels, 40 and 42, can form part of the front waist edge 22 of the absorbent article 10, and the waist end edges 50 of the back side panels, 44 and 46, can form part of the back waist edge 24 of the absorbent article 10.

The front side panels, 40 and 42, and back side panels, 44 and 46, can include an elastic material capable of stretching laterally. Suitable elastic materials, as well as one described process for incorporating elastic front side panels, 40 and 42, and back side panels, 44 and 46, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 40 and 42, and back side panels, 44 and 46, may include other woven or non-woven materials, such as those described above as being suitable for the outer cover 26 or bodyside liner 28, mechanically pre-strained composites, or stretchable but inelastic materials.

Figure 7:
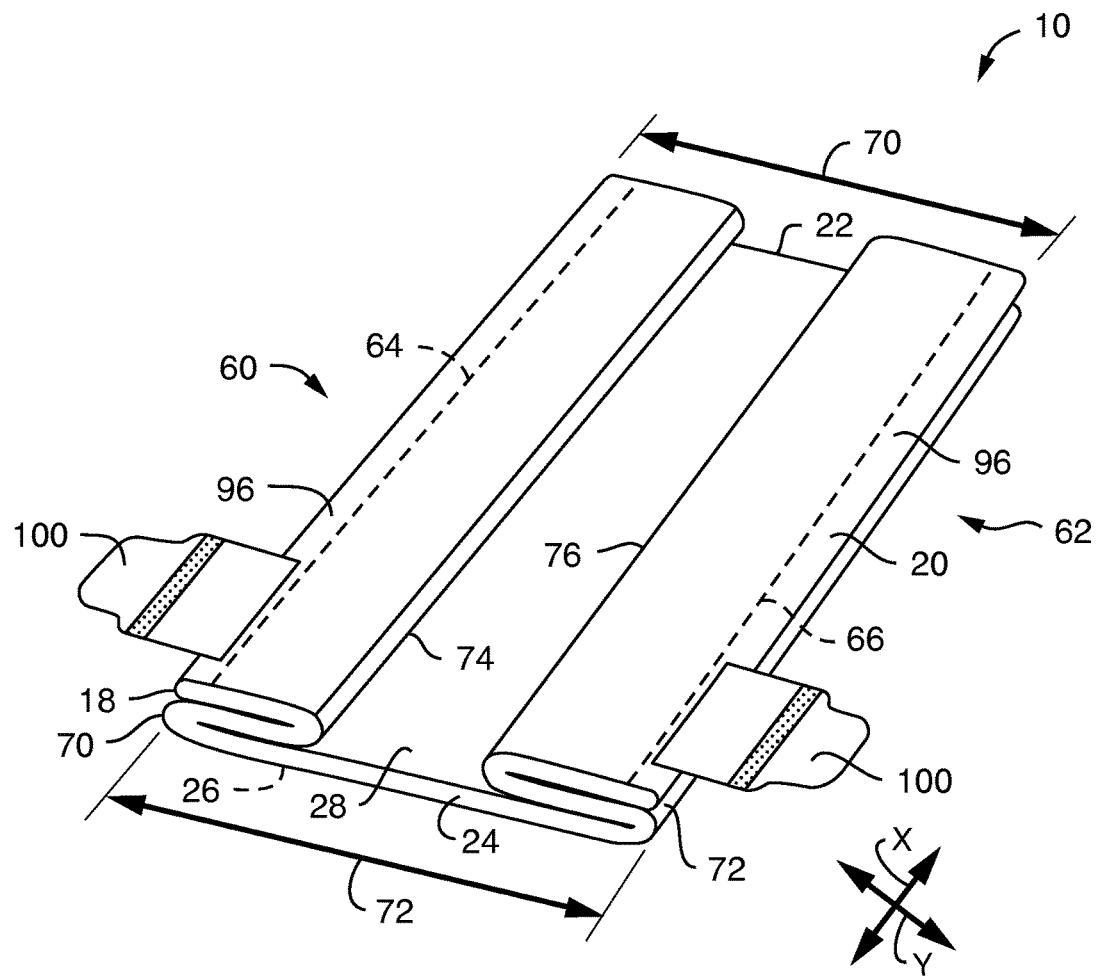
FIG. 7 is a perspective view of an embodiment of an absorbent article.

Fastening System:

In various embodiments, such as, for example, embodiments in which the absorbent article 10 can be, for example, a diaper or an adult incontinence garment, the absorbent article 10 can include a fastener system (such as illustrated in FIG. 7). The fastener system can include one or more back fasteners 100 and one or more front fasteners. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 100 can include one or more materials bonded together to form a composite ear as is known in the art. For example, the composite fastener may be composed of a stretch component, a nonwoven carrier or hook base, and a fastening component. The front fastener can be located on the garment facing surface of the outer cover 26 in the front waist region 12 of the absorbent article 10 and can be any component capable of engaging the back fasteners 100.

Fluid Transfer Layer:

In an embodiment, the absorbent article 10 can have a fluid transfer layer (not shown). The fluid transfer layer can have a wearer facing surface and a garment facing surface. In an embodiment, the garment facing surface of the fluid transfer layer can be bonded to the wearer facing surface of the absorbent body 30. Bonding of the garment facing surface of the fluid transfer layer to the wearer facing surface of the absorbent body 30 can occur through the use of adhesive. In an embodiment, the fluid transfer layer can completely encompass the absorbent body 30 and can be sealed to itself. In an embodiment, the fluid transfer layer may be folded over on itself and then sealed using, for example, heat and/or pressure. In an embodiment, the fluid transfer layer may be composed of separate sheets of material which can be utilized to partially or fully encompass the absorbent body 30 and which can be sealed together using a sealing means such as an ultrasonic bonder or other thermochemical bonding means or the use of an adhesive.

In an embodiment, the fluid transfer layer can be bonded with only the wearer facing surface of the absorbent body 30. In an embodiment, the fluid transfer layer can be bonded with the wearer facing surface and at least one of the edges, 32, 34, 36 and/or 38, of the absorbent body 30. In an embodiment, the fluid transfer layer can be bonded with the wearer facing surface, at least one of the edges, 32, 34, 36 and/or 38, and the garment facing surface of the absorbent body 30. In an embodiment, the absorbent body 30 may be partially or completely encompassed by the fluid transfer layer.

The fluid transfer layer can be pliable, less hydrophilic than the absorbent body 30, and sufficiently porous to be liquid permeable to thereby permit liquid to penetrate through its thickness to reach the absorbent body 30. In an embodiment, the fluid transfer layer can have sufficient structural integrity to withstand wetting thereof and of the absorbent body 30. In an embodiment, the fluid transfer layer can be constructed from a single layer of material or it may be a laminate constructed from two or more layers of material.

A common fluid transfer layer is an absorbent cellulosic material such as creped wadding or a high-strength tissue. A disadvantage of this common type of fluid transfer layer is a deficiency of wet strength to maintain structural integrity of the absorbent body 30. In an embodiment, the fluid transfer layer can be a laminate of a meltblown nonwoven material having fine fibers, laminated to at least one, spunbond nonwoven material layer having coarse fibers. In such an embodiment, the fluid transfer layer can be a spunbond-meltblown ("SM") material. In an embodiment, the fluid transfer layer can be a spunbond-meltblown-spunbond ("SMS") material. A non-limiting example of such a fluid transfer layer can be a 10 gsm spunbond-meltblown-spunbond material. In an embodiment, the fluid transfer layer can be composed of at least one material which has been fluid entangled into a nonwoven substrate. In an embodiment, the fluid transfer layer can be composed of at least two materials which have been fluid entangled into a nonwoven substrate. In an embodiment, the fluid transfer layer can have at least three materials which have been fluid entangled into a nonwoven substrate. A non-limiting example of a fluid transfer layer can be a 33 gsm fluid entangled substrate. In such an example, the fluid transfer layer can be a 33 gsm fluid entangled substrate composed of a 12 gsm spunbond material, a 10 gsm wood pulp material having a length from about 0.6 cm to about 5.5 cm, and an 11 gsm polyester staple fiber material. To manufacture the fluid transfer layer just described, the 12 gsm spunbond material can provide a base layer while the 10 gsm wood pulp material and the 11 gsm polyester staple fiber material can be homogeneously mixed together and deposited onto the spunbond material and then fluid entangled with the spunbond material. In an embodiment, a wet strength agent can be included in the fluid transfer layer. A non-limiting example of a wet strength agent can be Kymene 6500 (557LK) or equivalent available from Ashland Inc. of Ashland, Ky., U.S.A.

In an embodiment, the fluid transfer layer can be bonded with an absorbent body 30 which is made at least partially of particulate material such as superabsorbent material. In an embodiment in which the fluid transfer layer at least partially or completely encompasses the absorbent body 30, the fluid transfer layer should not unduly expand or stretch as this might cause particulate material to escape from the absorbent body 30. In an embodiment, the fluid transfer layer, while in a dry state, should have respective elongation values at peak load in the machine and cross directions of 30 percent or less and 40 percent or less. In an embodiment, the fluid transfer layer may have a longitudinal length the same as the longitudinal length of the absorbent body 30.

In an embodiment, the fluid transfer layer can have a basis weight less than about 40 gsm. In an embodiment, the fluid transfer layer can have a basis weight less than about 40, 39, 38, 37, 36, 35, 34, 33, 32, 31, 30, 25, 20, 15, or 10 gsm. In an embodiment, the fluid transfer layer can have a basis weight from about 10, 15, 20, 25, or 30 gsm to about 31, 32, 33, 34, 35, 36, 37, 38, 39, or 40 gsm Acquisition Layer:

In an embodiment, the absorbent article 10 can have an acquisition layer (not shown). The acquisition layer can help decelerate and diffuse surges or gushes of liquid body waste penetrating the bodyside liner 28. In an embodiment, the acquisition layer can be positioned between the bodyside liner 28 and the absorbent body 30 to take in and distribute urine for absorption by the absorbent body 30. In an embodiment, the acquisition layer can be positioned between the bodyside liner 28 and a fluid transfer layer.

The acquisition layer may have any longitudinal length dimension as deemed suitable. The acquisition layer may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer can have any length such that the acquisition layer can be coterminous with the waist edges, 22 and 24, of the absorbent article 10. In an embodiment, the longitudinal length of the acquisition layer can be the same as the longitudinal length of the absorbent body 30. In such an embodiment the midpoint of the longitudinal length of the acquisition layer can substantially align with the midpoint of the longitudinal length of the absorbent body 30.

In an embodiment, the longitudinal length of the acquisition layer can be shorter than the longitudinal length of the absorbent body 30. In such an embodiment, the acquisition layer may be positioned at any desired location along the longitudinal length of the absorbent body 30. As an example of such an embodiment, the absorbent article 10 may contain a target area 152 where repeated liquid surges typically occur in the absorbent article 10. The particular location of a target area can vary depending on the age and gender of the wearer of the absorbent article 10. For example, males tend to urinate further toward the front end of the absorbent article 10 and the target area may be phased forward within the absorbent article 10. For example, the target area for a male wearer may be positioned about 2¾" forward of the midpoint of the absorbent body 30 and may have a length of about ±3" and a width of about ±2". The female target area can be located closer to the center of the crotch region 18 of the absorbent article 10. For example, the target area for a female wearer may be positioned about 1" forward of the midpoint of the absorbent body 30 and may have a length of about ±3" and a width of about ±2". As a result, the relative longitudinal placement of the acquisition layer within the absorbent article 10 can be selected to best correspond with the actual target area of either or both categories of wearers. In an embodiment, the absorbent article 10 may contain a target area centered within the crotch region 18 of the absorbent article 10 with the premise that the absorbent article 10 would be worn by a female wearer. The acquisition layer, therefore, may be positioned along the longitudinal length of the absorbent article 10 such that the acquisition layer is substantially aligned with the target area of the absorbent article 10 intended for a female wearer. Alternatively, the absorbent article 10 may contain a target area positioned between the crotch region 18 and the front waist region 12 of the absorbent article 10 with the premise that the absorbent article 10 would be worn by a male wearer. The acquisition layer, therefore, may be positioned along the longitudinal length of the absorbent article 10 such that the acquisition layer is substantially aligned with the target area of the absorbent article 10 intended for a male wearer. In an embodiment, the acquisition layer can have a size dimension that is the same size dimension as the target area of the absorbent article 10 or a size dimension greater than the size dimension of the target area of the absorbent article 10.

The acquisition layer may have any width as desired. The acquisition layer may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer may vary dependent upon the size and shape of the absorbent article 10 within which the acquisition layer will be placed. The acquisition layer can have a width smaller than, the same as, or larger than the width of the absorbent body 30. Within the crotch region 16 of the absorbent article 10, the acquisition layer can have a width smaller than, the same as, or larger than the width of the absorbent body 30.

In an embodiment, the acquisition layer can be a through-air bonded-carded web such as a 35 gsm through-air bonded-carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP 6d), about 35% Huvis N-215 (PE/PP 2d), and about 30% Huvis SD-10 PET 6d, or equivalent composite, available from SamBo Company, Ltd, Korea.

The acquisition layer may have additional parameters including basis weight and thickness. In an embodiment, the basis weight of the acquisition layer can be at least about 20 gsm. In an embodiment, the basis weight of the acquisition layer can be from about 20, 30, 40, 50 or 60 gsm to about 65, 70, 75, 80, 85, 90, 100 gsm. In an embodiment, the basis weight of the acquisition layer can be less than about 100, 90, 85, 80, 75, 70, 65, 60 or 50 gsm. In an embodiment, the acquisition layer can have a thickness, measured at 0.05 psi, of less than about 1.5 mm. In an embodiment, the acquisition layer can have a thickness, measured at 0.05 psi, of less than about 1.5, 1.25, or 1.0 mm.

Waist Elastic Members:

In an embodiment, the absorbent article 10 can have waist elastic members which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members may be omitted from the absorbent article 10 without departing from the scope of this disclosure.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. an outer cover and a bodyside liner bonded to the outer cover;
   b. an absorbent body positioned between the outer cover and the bodyside liner;
   c. a front waist region having a front waist edge, a back waist region having a back waist edge, and a crotch region interconnecting the front waist region to the back waist region;
   d. a pair of laterally opposed front side panels and a pair of laterally opposed back side panels, each pair of side panels being bonded to the respective front and back waist regions and each front side panel being bonded to one of the back side panels by an engagement seam; ("e", "f" and "g" were "d", "e" and "f")
   e. a pair of opposing longitudinal direction folded side regions extending from the front waist edge to the back waist edge, each longitudinal direction side region comprising at least one longitudinal direction fold and a portion of each of the longitudinal direction folded side regions is bonded to at least a portion of the bodyside liner in the front waist region;
   f. a first configuration in which a lateral direction width of the front waist edge is the same as a lateral direction width of the back waist edge; and
   g. a second configuration in which the lateral direction width of the front waist edge is smaller than the lateral direction width of the back waist edge.

2. The absorbent article of claim 1 wherein each of the longitudinal direction folded side regions is unbonded to the bodyside liner in at least one of the back waist region or the crotch region.

3. The absorbent article of claim 1 wherein each of the longitudinal direction folded side regions comprises at least one elastic member.

4. The absorbent article of claim 1 wherein each of the longitudinal direction folded side regions comprises at least a portion of the outer cover.

5. The absorbent article of claim 1 wherein each of the longitudinal direction folded side regions comprises at least a portion of the outer cover and bodyside liner.

6. The absorbent article of claim 1 wherein a ratio of the lateral direction width of the front waist edge to the lateral direction width of the back waist edge is 0.5 when the absorbent article is in the second configuration.

7. An absorbent article comprising:
   a. an outer cover and a bodyside liner bonded to the outer cover;
   b. an absorbent body positioned between the outer cover and the bodyside liner;
   c. a front waist region having a front waist edge, a back waist region having a back waist edge, and a crotch region interconnecting the front waist region to the back waist region;
   d. a pair of laterally opposed front side panels and a pair of laterally opposed back side panels, each pair of side panels being bonded to the respective front and back waist regions and each front side panel being bonded to one of the back side panels by an engagement seam; ("e", "f" and "g" were "d", "e" and "f")
   e. a pair of opposing longitudinal direction folded side regions extending from the front waist edge to the back waist edge, each longitudinal direction side region comprising at least one longitudinal direction fold and a portion of each of the longitudinal direction folded side regions is bonded to at least a portion of the bodyside liner in the front waist region;
   f. a first configuration in which a ratio of a lateral direction width of the front waist edge to a lateral direction width of the back waist edge is 1; and
   g. a second configuration in which a ratio of the lateral direction width of the front waist edge to the lateral direction width of the back waist edge is less than 1.

8. The absorbent article of claim 7 wherein each of the longitudinal direction folded side regions is unbonded to the bodyside liner in at least one of the back waist region or the crotch region.

9. The absorbent article of claim 7 wherein each of the longitudinal direction folded side regions comprises at least one elastic member.

10. The absorbent article of claim 7 wherein each of the longitudinal direction folded side regions comprises at least a portion of the outer cover.

11. The absorbent article of claim 7 wherein each of the longitudinal direction folded side regions comprises at least a portion of the outer cover and bodyside liner.

12. The absorbent article of claim 7 wherein a ratio of the lateral direction width of the front waist edge to the lateral direction width of the back waist edge is 0.5 when the absorbent article is in the second configuration.

13. An absorbent article comprising:
   a. an outer cover and a bodyside liner bonded to the outer cover;
   b. an absorbent body positioned between the outer cover and the bodyside liner;
   c. a front waist region having a front waist edge, a back waist region having a back waist edge, and a crotch region interconnecting the front waist region to the back waist region;
   d. a pair of laterally opposed front side panels and a pair of laterally opposed back side panels, each pair of side panels being bonded to the respective front and back waist regions and each front side panel being bonded to one of the back side panels by an engagement seam; ("e", "f" and "g" were "d", "e" and "f")
   e. a pair of opposing longitudinal direction folded side regions extending from the front waist edge to the back waist edge, each longitudinal direction side region comprising at least two longitudinal direction folds and a portion of each longitudinal direction folded side regions is bonded to at least a portion of the bodyside liner in the front waist region;
   f. a first configuration in which a ratio of a lateral direction width of the front waist edge to a lateral direction width of the back waist edge is 1; and
   g. a second configuration in which a ratio of the lateral direction width of the front waist edge to the lateral direction width of the back waist edge is 0.5.

14. The absorbent article of claim 13 wherein each of the longitudinal direction folded side regions is unbonded to the bodyside liner in at least one of the back waist region or the crotch region.

15. The absorbent article of claim 13 wherein each of the longitudinal direction folded side regions comprises at least one elastic member.

16. The absorbent article of claim 13 wherein each of the longitudinal direction folded side regions comprises at least a portion of the outer cover.

17. The absorbent article of claim 13 wherein each of the longitudinal direction folded side regions comprises at least a portion of the outer cover and bodyside liner.

\* \* \* \* \*